United States Patent [19]

Kalawsky

[11] Patent Number: 5,396,329
[45] Date of Patent: Mar. 7, 1995

[54] POLARISATION IMAGE DETECTION SYSTEMS

[75] Inventor: Roy S. Kalawsky, Brough, England

[73] Assignee: British Aerospace PLC, London, England

[21] Appl. No.: 163,568

[22] Filed: Jan. 25, 1988

[30] Foreign Application Priority Data

Jan. 23, 1987 [GB] United Kingdom ............... 8701521

[51] Int. Cl.⁶ ..................... G01J 4/00; G02F 1/01
[52] U.S. Cl. ........................... 356/364; 250/225; 356/367
[58] Field of Search ............ 356/364, 365, 366, 367, 356/369, 370; 250/225

[56] References Cited

U.S. PATENT DOCUMENTS

| | | | |
|---|---|---|---|
| 3,450,478 | 6/1969 | Sebestyen | 356/365 |
| 3,612,688 | 10/1971 | Liskowitz | 356/365 |
| 3,927,945 | 12/1975 | Bates | 356/366 |
| 3,985,447 | 10/1976 | Aspnes | 356/369 |
| 4,523,848 | 6/1985 | Gorman et al. | 356/369 |
| 4,624,563 | 11/1986 | Johnson | 356/365 |
| 4,626,100 | 12/1986 | Johnson | 356/365 |

FOREIGN PATENT DOCUMENTS

| | | |
|---|---|---|
| 1034262 | 6/1966 | United Kingdom . |
| 1413413 | 11/1975 | United Kingdom . |
| 1419738 | 12/1975 | United Kingdom . |
| 1459410 | 12/1976 | United Kingdom . |
| 2044444 | 10/1980 | United Kingdom . |
| 2181540 | 4/1987 | United Kingdom . |

Primary Examiner—Stephen C. Buczinski
Attorney, Agent, or Firm—Cushman, Darby & Cushman

[57] ABSTRACT

Known polarization image detection systems produce an image illustrating structural information of a viewed scene which is representative of the degree of linear polarization. The present invention describes an improved detector system which enables more information to be extracted from the scene. The system comprises an optical arrangement having an optical axis (4) about which a retarder (1) and a linear polarizer (2) can be independently rotated, for producing a focussed image on a detector. This arrangement can be expressed mathematically in terms of Stokes parameters and Mueller matrices, and the expression can then be solved to provide three different polarization images representative of the viewed scene.

18 Claims, 4 Drawing Sheets

POLARISATION IMAGE DETECTION SYSTEMS

BACKGROUND TO THE INVENTION

The present invention relates to polarisation image detection systems.

Most of the light that reaches our eyes or man-made sensors comes indirectly through scattering. An object is usually viewed by observing the scattered light that is reflected from the object's surface. Scattering is the observable interaction between light and matter and occurs at all wavelengths in the electromagnetic spectrum. These scattering processes are fundamental to the production of polarisation in the universe.

When light or any form of electromagnetic radiation is reflected from a surface it may become polarised, the type and degree of polarisation being a function of angle of incidence, surface structure/texture and material type. Certain materials can also alter the polarisation state of electromagnetic radiation passing through them. These materials are known as optically active materials.

A polarisation image detector forms an image signal indicating variations in optical polarisation of light from a scene. When the signal is reproduced as a picture on a television screen, it illustrates surface structure of the scene rather than reflected intensity or colour. Polarisation image detectors may be used in a number of fields, for example in microscopy, medical diagnosis, meteorology and so on.

A known polarisation image detector described in British Patent Specification 1472854 comprises two television camera tubes which receive light via a beam splitter comprising a partially reflecting mirror and via respective polarisers of which the polarising directions are set at right angles to one another. After gamma correction to compensate for non-linearities of the camera system, the video signals are combined to form a polarisation representative picture signal.

In another known form of polarisation image detector, instead of two camera tubes, there can be used a single tube having two separate photo-sensitive screens or there can be used a single camera with a single screen in association with a polariser, for example a rotating polarising plate or an electro-optic crystal, operable to change periodically the polarisation direction of the light received by the camera, and with signal delay means operable to bring the signals obtained during the respective periods into synchronism.

In our earlier patent application No. 8125282, we describe a polarising image detector comprising polarising means for receiving optical radiation from a scene and for forming images of the scene respectively constituted by radiation components which differ in respect of the polarisation thereof, two charge-coupled area imaging devices for forming electrical picture signals corresponding to said images, and means for combining said picture signals to form a signal containing information about the polarisation of the optical radiation from the scene.

One example of our earlier invention was described in which the means for receiving optical radiation from the scene and for forming separate images with different polarisation comprised a Wollaston block double image prism and lens arrangement. This arrangement split the partially polarised light received from the scene into two orthogonally polarised images which are focussed onto two separate charge-coupled devices (CCDs). The electrical picture signals produced by these CCDs are summed and subtracted, and a signal representing the division of their subtraction by their sum is applied to a television receiver or stored on a video recorder or further processed by a data processor to give structural information concerning every point on the scene as opposed to colour or brightness information produced by a conventional television arrangement.

In other examples described in our earlier patent application, the Wollaston block is replaced by a Glan-Thompson prism. Various alternative arrangements are described in which, for example, the electrical picture signals produced by the charge-coupled devices are digitised by analogue-to-digital converters and processed by computer to form the required polarisation-dependent image data. The advantage of the latter arrangement is that known digital techniques for image enhancement or recognition could then be applied to the data to improve the quality of the polarisation-dependent image data extracted. These earlier systems are only capable of resolving linear polarisation forms.

It is an objective of the present invention to provide a polarisation image detection system which can resolve all forms of polarisation information emanating from a scene or object under examination. The new system can produce three different types of image representing the polarisation factor, degree of polarisation and polarisation phase angle for elliptically polarised light. It should be noted that elliptical polarisation includes all polaristaion types; linear and circular polarisation forms are just two specific cases of elliptical polarisation.

SUMMARY OF THE INVENTION

According to the present invention, there is provided a polarisation image detection system comprising a lens system having an optical axis and arranged for receiving incident radiation from a viewed scene and for producing a focussed image thereof, detector means positioned on the optical axis at a focussed image location, linear polariser means and retarder means both located on the optical axis and each having a maximum electric vector direction associated therewith transverse to the optical axis, and means for varying the properties of the system by doing at least one of a) rotating the electric vector direction of the polariser means relative to the detector means, b) rotating the electric vector direction of the retarder means relative to the detector means, and c) varying the retardance of the retarder means.

Advantageously, the retardance of the retarder means and the orientation of the linear polariser means are fixed, and the retarder means is rotatable about the optical axis to give a plurality of intensity images of the viewed scene.

By having either or both the polariser means and the retarder means rotatable about the optical axis, it is possible to extract all polarisation image information from the scene. This could also be done by varying the retardance of the retarder, for example by using a Babinet or Soleil compensator. In particular three different polarisation images can be obtained which correspond to a viewed scene, namely, the degree of polarisation, the polarisation factor and the polarisation phase angle.

The behaviour of light in a polarisation image detector including a polariser and a retarder both rotatable about optical axis can be described in known fashion using a combination of Stokes parameters and Mueller matrices thus:

|  | Emergent radiation | Linear polariser | conversion of retarder radiation to polariser axis | retarder | conversion of incident radiation to retarder axis | incident radiation |
|---|---|---|---|---|---|---|

$$\begin{bmatrix} I' \\ Q' \\ U' \\ V' \end{bmatrix} = \frac{1}{2} \begin{bmatrix} 1 & 1 & 0 & 0 \\ 1 & 1 & 0 & 0 \\ 0 & 0 & 0 & 0 \\ 0 & 0 & 0 & 0 \end{bmatrix} \begin{bmatrix} 1 & 0 & 0 & 0 \\ 0 & \cos 2(\alpha-\beta) & \sin 2(\alpha-\beta) & 0 \\ 0 & -\sin 2(\alpha-\beta) & \cos 2(\alpha-\beta) & 0 \\ 0 & 0 & 0 & 1 \end{bmatrix} \begin{bmatrix} 1 & 0 & 0 & 0 \\ 0 & 1 & 0 & 0 \\ 0 & 0 & \cos r & \sin r \\ 0 & 0 & -\sin r & \cos r \end{bmatrix} \begin{bmatrix} 1 & 0 & 0 & 0 \\ 0 & \cos 2\beta & \sin 2\beta & 0 \\ 0 & -\sin 2\beta & \cos 2\beta & 0 \\ 0 & 0 & 0 & 1 \end{bmatrix} \begin{bmatrix} I \\ Q \\ U \\ V \end{bmatrix}$$

In this equation I, Q, U and V are the Stokes parameters for light incident on the system, I being the intensity of light reflected or scattered from the surface being viewed.

BRIEF DESCRIPTION OF THE DRAWINGS

An embodiment of the invention will now be described, by way of example only, with reference to the accompanying drawings in which:

FIG. 2A illustrates a modification of the FIG. 2 arrangement.

PREFERRED EMBODIMENT OF THE INVENTION

It should be noted that although the invention is described with reference to an optical arrangement, by substitution of components it is possible to produce other devices according to the invention which operate in other regions of the electromagnetic spectrum.

Figure 1:
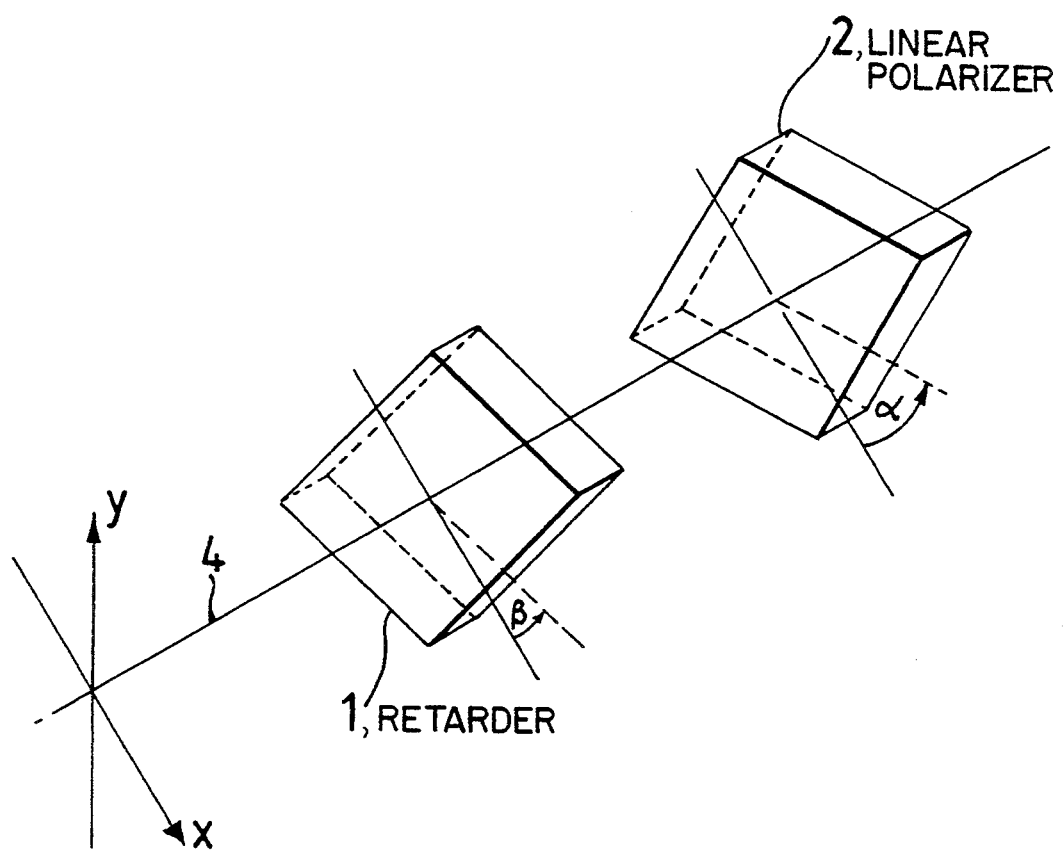
FIG. 1 is a diagrammatic view of part of an optical system of a polarisation image detector.

FIG. 1 shows a retarder 1 having a retardance r and a linear polariser 2 aligned on an optical axis 4. The retarder 1 and the polariser 2 are independently rotatable about the axis 4 and are shown forming respective angles and with a fixed reference. The fixed reference in this case is taken as the direction of the electric vector or eigenvector of the polariser 2 which is parallel to OX on the axes shown.

Figure 2:
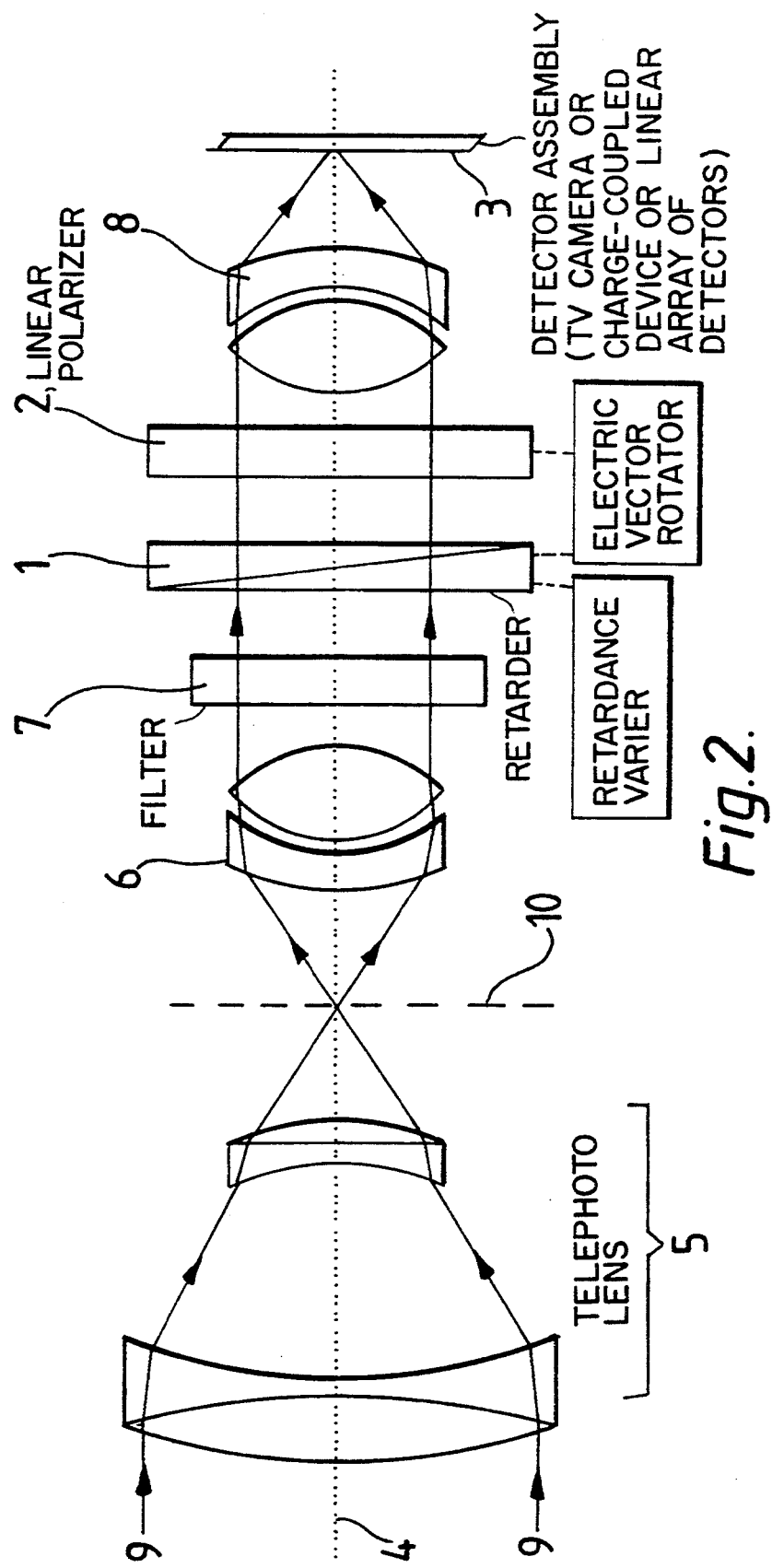
FIG. 2 is an optical ray diagram illustrating the operation of a optical polarisation image detector according to the invention.
Figure 5:
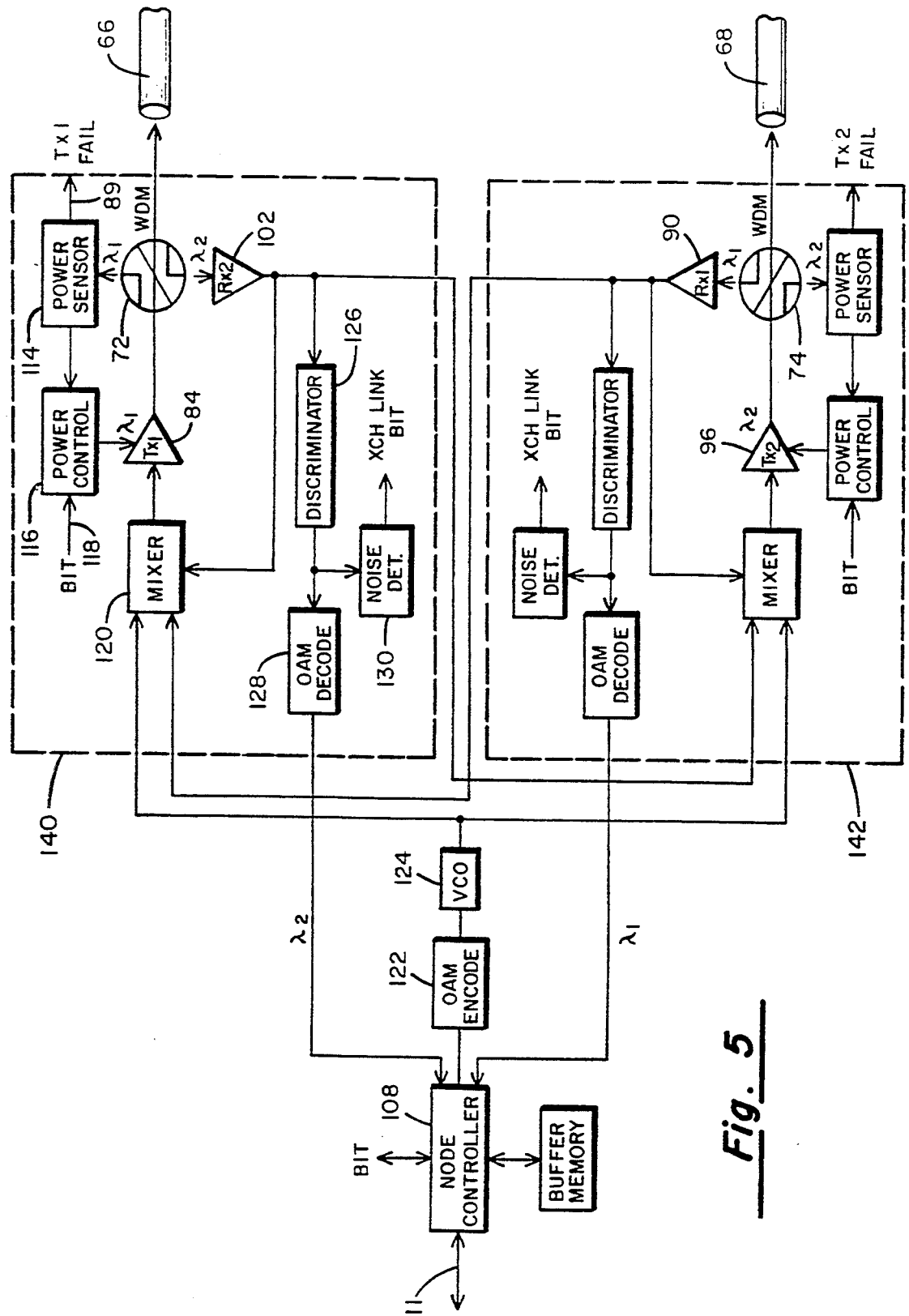

FIG. 2 shows diagrammatically the retarder 1 and polariser 2 mounted in a practical polarisation image detector. Incoming radiation 9 from a viewed scene is focussed onto an image plane 10 by a telephoto lens arrangement 5. The radiation at the image plane 10 is then collimated by an achromatic doublet lens 6. Collimated radiation passes through the retarder 1 and polariser 2 before being focussed onto a detector assembly 3 by a second achromatic doublet lens 8. If non-monochromatic radiation is being viewed, a filter 7 is included prior to the retarder 1 to limit the radiation being passed through the rest of the image detector.

The detector assembly 3 measures the intensity of the polarised radiation incident on it. The assembly can be an array of detectors which is scanned across the image, for example, a linear array comprising a line of detectors. Alternatively, an "area" detector such as a television camera or a charge-coupled device, may be used. The detector must have an adequate resolution so that unambiguous data is obtained, for example, a resolution of two hundred and fifty six grey levels.

The image produced corresponding to the viewed scene may be viewed directly or may be further processed to provide more information relating to the viewed scene using either a digital computer or a dedicated analogue computer.

The optical system can be represented in terms of Mueller matrices, one for each component:

|  | Emergent radiation | Linear polariser | conversion of retarder radiation to polariser axis | retarder | conversion of incident radiation to retarder axis | incident radiation |
|---|---|---|---|---|---|---|

$$\begin{bmatrix} I' \\ Q' \\ U' \\ V' \end{bmatrix} = \frac{1}{2} \begin{bmatrix} 1 & 1 & 0 & 0 \\ 1 & 1 & 0 & 0 \\ 0 & 0 & 0 & 0 \\ 0 & 0 & 0 & 0 \end{bmatrix} \begin{bmatrix} 1 & 0 & 0 & 0 \\ 0 & \cos 2(\alpha-\beta) & \sin 2(\alpha-\beta) & 0 \\ 0 & -\sin 2(\alpha-\beta) & \cos 2(\alpha-\beta) & 0 \\ 0 & 0 & 0 & 1 \end{bmatrix} \begin{bmatrix} 1 & 0 & 0 & 0 \\ 0 & 1 & 0 & 0 \\ 0 & 0 & \cos r & \sin r \\ 0 & 0 & -\sin r & \cos r \end{bmatrix} \begin{bmatrix} 1 & 0 & 0 & 0 \\ 0 & \cos 2\beta & \sin 2\beta & 0 \\ 0 & -\sin 2\beta & \cos 2\beta & 0 \\ 0 & 0 & 0 & 1 \end{bmatrix} \begin{bmatrix} I \\ Q \\ U \\ V \end{bmatrix} \quad (1)$$

where I, Q, U and V are the Stokes parameters for the incident radiation, I being the intensity of the incident radiation (radiation scattered from the viewed scene), and Q, U and V specifying states of polarisation, that is, linear polarisation with a horizontal preference, linear polarisation with a 45° preference, and the shape of the polarisation ellipse and handedness for the incident radiation respectively. If V=O, no circular polarisation is present. I', Q', U' and V' are the corresponding Stokes parameters for the radiation incident on the detector assembly 3 emerging from the lens system.

It should be noted that in some text books, the Stokes parameters are referenced as $S_o$, $S_1$, $S_2$ and $S_3$.

If the system is to measure the intensity of the emergent radiation the equation (1) above reduces to:

$$I' = \tfrac{1}{2}[I + (Q \cos 2\beta + U \sin 2\beta) \cos 2(\alpha-\beta) + [(U \cos 2\beta - Q \sin 2\beta) \cos r + V \sin r] \sin 2(\alpha-\beta)] \quad (2)$$

If the retardance r is known and fixed at $r = \lambda/4$, the equation (2) becomes simplified:

$$I' = \tfrac{1}{2}[I + (Q \cos 2\beta + U \sin 2\beta) \cos 2(\alpha-\beta) + V \sin 2(\alpha-\beta)] \quad (3)$$

The variable parameters for the described system viewing a given scene are $\alpha$, $\beta$ and r. In the cases of equations (1) and (2), two parameters are chosen and maintained constant while the third is varied. A series of intensity values are obtained which can be used to solve for I, Q, U and V and consequently I', Q', U' and V' can be determined. In the case of equation (3), r is fixed so either $\alpha$ or $\beta$ is fixed and the other varied.

Once I, Q, U and V are determined, the following equations can be evaluated:

(a) degree of polarisation, p $$p = \sqrt{\frac{Q^2 + U^2 + V^2}{I}} \quad (4)$$

(b) polarisation factor, $p_f$ $$p_f = Q/I \quad (5)$$

and (c) polarisation phase angle, $\theta$ $$\theta = \tfrac{1}{2}\tan^{-1}(U/Q) \quad (6)$$

The solutions to these equations can be used to produce images corresponding to the degree of polarisation, polarisation factor, and polarisation phase angle for a given scene.

Off-axis effects due to the incident radiation not being parallel to the optical axis 4 are avoided by using the doublet lenses 6 and 8 to collimate and focus the light.

The operating wavelength of the polarisation image detector determines the optical elements used. For example, operation in the visible or near infra-red part of the spectrum will require a crystalline quartz retarder and either a dichroic polariser or one of the many prism polarisers. The materials used for the optical elements are chosen to optimise the response of the detector.

A reduction in processing of the detected image can be achieved if a Wollaston prism (FIG. 2A) is used in place of the linear polariser because of its ability to resolve a beam of linearly polarised light into two orthogonal beams, each of which can then be incident on a respective detector 3, 3' through lens 8, 8'. This enables the intensity I to be determined, using the first Stokes parameter directly i.e. $S_0 = a^2 + b^2$.

An achromatic retarder is preferred for the retarder 1, but these devices are extremely expensive. Alternatively, a cheaper monochromatic retarder can be used provided that the incoming radiation is passed through a suitable bandpass filter 7 before passing through the retarder. The filter is necessary because monochromatic retarders exhibit different retardances at different wavelengths. It is preferred that ionic absorption filters are used in preference to interference filters. This is because there is a tendency for the interference filter to introduce appreciable polarisation into the radiation beam passing through it.

Achromatic doublets are preferred for monochromatic use because they can reduce the aberrations that would be present in single lenses.

If the electromagnetic radiation emanating from the scene is collimated that is, parallel to the optical axis 4, then the first collimating lens can be omitted from the system.

Operation of the polarisation detector at infra-red wavelengths requires the use of a different polariser 2, typically a wire grid or grating polariser. The spacing between the grid or diffraction grating may vary from 0.347 μm to 317 μm depending on the wavelength used. The polariser could even be a reflection type, for example, a germanium plate could be used.

Systems operating with radar-wavelength incident radiation would generally employ wire grids as the polariser element.

The operating wavelengths will determine the choice of detector 3. It must be stressed that many common detectors exhibit polarisation sensitivity with a resulting response that varies according to the orientation of the incident radiation. Photomultiplier tubes for example, suffer from this effect.

Semiconductor sensor arrays probably form the best sensors, however it is necessary to consider the manner in which they have been constructed. Interline transfer charge-coupled devices have prominent line structures due to their method of operation and may act as a polariser at certain wavelengths. Frame transfer charge-coupled devices do not appear to exhibit this effect.

Whilst it is desirable to use area imaging systems for example, CCDs in conjunction with the polarisation image detector described above, it should be noted that it is perfectly feasible to use a single or line of detectors and scan the image over the detector(s). Generally, mechanical scanning assemblies will be used in these applications and therefore great care must be taken with the inclusion of beam deflecting mirrors because these quite often modify the polarisation of the beam. An array of detectors tends to suffer from varying response from one detector to another whilst a single detector systems avoids this problem. Modern computer based image processing systems are usually able to cope with a varying response and so this is no longer a serious problem for array systems.

Figure 3:
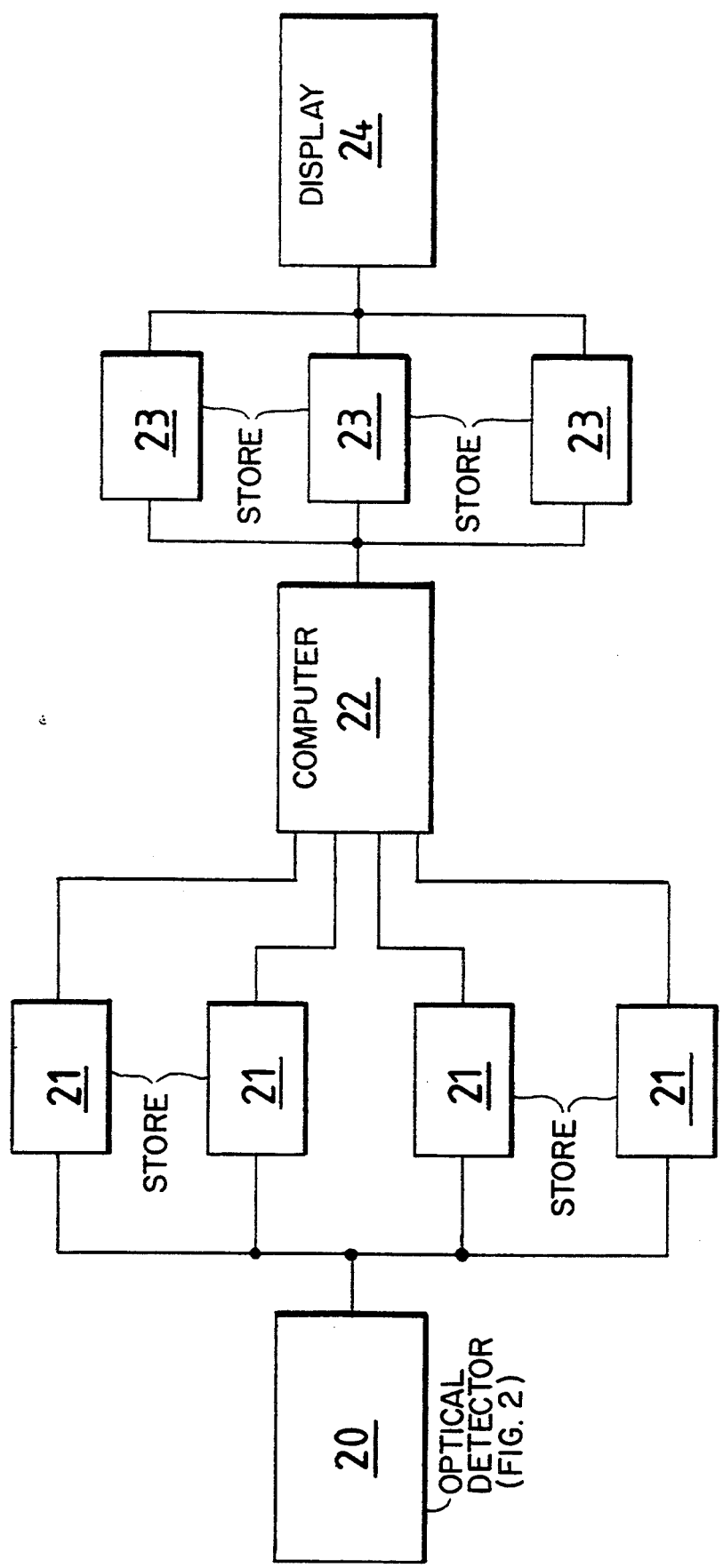
FIG. 3 is a schematic block diagram of a processing arrangement which can be used with the detector of FIG. 2 or 2A.

FIG. 3 shows a schematic block diagram of one embodiment of a processing arrangement for the detection system. The optical arrangement, including the detector, of FIG. 2 is shown generally at 20. If the retardance, r, and the angle of the polariser to the fixed reference OX, α, are fixed, the retarder 1 can be rotated about the optical axis to be in one of four positions, for example at 0°, 45°, 90° and 135° to the axis OX. The intensity of the viewed scene is measured with the retarder in each of these positions and each frame is stored in respective frame stores 21. A computer 22 is used to access the intensity values stored in each frame store 21 and to solve the equations as given above to produce the three different polarisation images. Each of these polarisation images is stored in a store 23 which is accessed, when required, to output the image of the viewed scene, for example on a display screen 24. The output need not be displayed, but could be used directly to control or initiate other processes.

The arrangement shown in FIG. 2 is typical of an optical form of a polarisation image detector according to the invention. Only minor alterations are required to produce analysers suitable for other wavelengths.

If the retardance is to be varied in the arrangement of FIG. 2, a Babinet or Soleil compensator can be used as the retarder.

Regardless of the operating wavelength used, the equations (1) to (6) above may be used to enable the desired images to be produced using a digital computer or a dedicated analogue computer for the requisite equation solving and image processing to produce a viewable result.

I claim:

1. A polarisation image detection system comprising:
   a lens system having an optical axis and arranged for receiving incident radiation from a viewed scene and for producing a focused image thereof;
   imaging detector means positioned on the optical axis at a focused image location for detecting and outputting a radiation level of said focused image;
   linear polarizer means and retarder means both located on the optical axis and each having a maximum electric vector direction associated therewith transverse to the optical axis;

means for varying the optical setting of the system by doing at least one of a) rotating the electric vector direction of the polarizer means relative to the detector means, b) rotating the electric vector direction of the retarder means relative to the detector means, and c) varying the retardance of the retarder means, the imaging detector means for detecting and outputting radiation levels of said focused image corresponding to said varied optical settings;

storage means for recording the outputs of the imaging detector means corresponding to the varied optical settings of the system; and computing means for calculating, from the recorded outputs, the degree of polarisation, the polarisation factor and the polarisation phase angle of the viewed scene.

2. A detection system according to claim 1, wherein the retardance of the retarder means and the orientation of the linear polariser means are fixed, and the retarder means is rotatable about the optical axis to give a plurality of intensity images of the viewed scene.

3. A detection system according to claim 1, wherein the linear polariser means and the retarder means are positioned between elements of the lens system.

4. A detection system according to claim 1, wherein the retarder means is an achromatic retarder device.

5. A detection system according to claim 1, wherein the retarder means is a monochromatic retarder device.

6. A detection system according to claim 5, wherein a bandpass filter is included prior to the monochromatic retarder.

7. A detection system according to claim 6, wherein the bandpass filter is an ionic absorption filter.

8. A detection system according to claim 1, wherein the lens system is optical and includes a telephoto lens arrangement.

9. A detection system according to claim 1, wherein the lens systems is optical and includes at least one achromatic doublet lens.

10. A detection system according to claim 9, wherein two achromatic doublets are provided, one on either side of the polariser-retarder combination.

11. A detection system according to claim 1, wherein the detector means comprises a television camera.

12. A detection system according to claim 1, wherein the detector means comprises an array of detector elements or pixels.

13. A detection system according to claim 12, wherein the array is a linear array which is scanned over the focussed image.

14. A detection system according to claim 12, wherein the array is an area array comprising a charge-coupled device.

15. A detection system according to claim 1, and including beam splitting means resolving the incident radiation into two orthogonal components and a second detector means.

16. A detection system according to claim 15, wherein the system operates at optical wavelengths and the beam splitting means is a Wollaston prism.

17. A detection system according to claim 1, wherein the processing means is a digital computer or a dedicated analogue computer.

18. A method of producing at least one polarisation image corresponding to a viewed scene using a polarisation detection system according to claim 1, the method comprising repeatedly varying at least one of a) the electric vector direction of the polariser means, b) the electric vector direction of the retarder means, and c) the retardance of the retarder means to obtain a set of images, and processing that set of images to produce the desired polarisation image(s).

* * * * *